United States Patent [19]
O'Brien et al.

[11] Patent Number: 6,123,749
[45] Date of Patent: Sep. 26, 2000

[54] SEPARATION OF $CO_2$ FROM UNSATURATED FLUORINATED COMPOUNDS BY SEMIPERMEABLE MEMBRANE

[75] Inventors: William G. O'Brien, Newark; Charles J. Noelke, Wilmington, both of Del.; Raymond C. Harker, Williamstown, N.J.; David John Van Bramer, Belpre, Ohio

[73] Assignee: E. I. du Pont de Nemours and Company, Wilmington, Del.

[21] Appl. No.: 09/071,026

[22] Filed: May 1, 1998

Related U.S. Application Data

[60] Provisional application No. 60/045,440, May 2, 1997.

[51] Int. Cl.⁷ .................................................. B01D 53/22
[52] U.S. Cl. ...................................................... 95/51; 95/45
[58] Field of Search ................................... 95/45, 51, 50

[56] References Cited

U.S. PATENT DOCUMENTS

| | | | |
|---|---|---|---|
| 4,879,396 | 11/1989 | Ozero | 549/534 |
| 4,990,168 | 2/1991 | Sauer et al. | 95/51 X |
| 5,042,992 | 8/1991 | Blinka et al. | 55/16 |
| 5,067,970 | 11/1991 | Wang et al. | 95/51 |
| 5,076,817 | 12/1991 | Hayes | 95/51 X |
| 5,085,676 | 2/1992 | Ekiner et al. | 55/158 |
| 5,085,774 | 2/1992 | Ekiner et al. | 210/500.23 |
| 5,105,270 | 4/1992 | Takahashi et al. | 358/113 |
| 5,120,329 | 6/1992 | Sauer et al. | 55/16 |
| 5,233,837 | 8/1993 | Callahan | 95/51 X |
| 5,234,471 | 8/1993 | Weinberg | 95/51 X |
| 5,345,013 | 9/1994 | Bramer et al. | 570/102 |
| 5,411,721 | 5/1995 | Doshi et al. | 95/51 X |
| 5,482,539 | 1/1996 | Callahan | 95/51 |
| 5,534,151 | 7/1996 | Lee | 95/45 X |
| 5,591,250 | 1/1997 | Stern et al. | 95/51 |
| 5,618,332 | 4/1997 | Ekiner et al. | 95/51 |
| 5,674,957 | 10/1997 | Desimone et al. | 526/89 |
| 5,702,503 | 12/1997 | Tse Tang | 95/51 X |
| 5,709,733 | 1/1998 | Hachisuka et al. | 95/51 |
| 5,730,779 | 3/1998 | Chernyakov et al. | 95/45 |
| 5,759,237 | 6/1998 | Li et al. | 95/45 X |
| 5,814,127 | 9/1998 | Li | 95/51 X |
| 5,855,647 | 1/1999 | Li et al. | 95/51 X |
| 5,858,065 | 1/1999 | Li et al. | 95/45 |
| 5,858,066 | 1/1999 | O'Brien et al. | 95/45 X |

FOREIGN PATENT DOCUMENTS

| | | |
|---|---|---|
| 0 128 506 | 12/1984 | European Pat. Off. . |
| 0 200 518 | 11/1986 | European Pat. Off. . |
| 0 373 683 | 6/1990 | European Pat. Off. . |
| 0 501 933 A2 | 2/1992 | European Pat. Off. . |
| 6-116180 | 10/1992 | Japan . |
| WO 95/32169 | 11/1995 | WIPO . |

OTHER PUBLICATIONS

Membranes can Efficiently Separate $CO_2$ From Mixtures, Schell et al., Oil & Gas Journal, Aug. 15, 1983, p. 83.

Relationship Between Gas Separation Properties and Chemical Structure in a Series of Aromatic Polyimides, Kim et al., Journal of Membrane Science, 37 (1988), 45–62.

*Primary Examiner*—Robert H. Spitzer

[57] ABSTRACT

A process for separating carbon dioxide from an unsaturated fluorinated compound carbon dioxide mixture comprising contacting the unsaturated fluorinated compound carbon dioxide mixture with a semipermeable membrane to form at least one exit stream having an increased concentration of carbon dioxide and at least one other exit stream having a reduced concentration of carbon dioxide.

5 Claims, 1 Drawing Sheet

SEPARATION OF CO₂ FROM UNSATURATED FLUORINATED COMPOUNDS BY SEMIPERMEABLE MEMBRANE

RELATED APPLICATIONS

This application claims the benefit of U.S. Provisional Application No. 60/045,440 filed May 2, 1997.

FIELD OF THE INVENTION

The present invention relates to a process for separating carbon dioxide from unsaturated fluorinated compounds such as fluoroalkyl perfluorovinyl ethers and other fluorinated compounds having a double bond.

BACKGROUND OF THE INVENTION

Fluoroalkyl perfluorovinyl ethers of the formula $R_f\text{—}CF_2\text{—}O\text{—}CF=CF_2$, wherein $R_f$ is fluorine or a fluorine-containing organic radical, have found extensive use as co-monomers for preparation of fluoroplastics and fluoroelastomers. Fluoroalkyl perfluorovinyl ethers are known to co-polymerize with alkenes such as ethylene, tetrafluoroethylene, chlorotrifluoroethylene, vinylidene fluoride, vinyl fluoride, propene and hexafluoropropene. Of particular interest and significant application are co-polymers formed by co-polymerization of perfluoroalkyl perfluorinated ethers with tetrafluoroethylene and/or hexafluoropropylene. These co-polymers are often referred to as perfluoroalkoxy co-polymers, and are useful in producing high-quality electrical insulation and molded components. A general review of perfluoroalkoxy co-polymers occurs in a review article titled "Organic Fluoropolymers" by Carlson et al, found in Ullman's Encyclopedia of Industrial Chemistry, Fifth Edition, p. 393.

The prevalent method found in the art for preparation of fluoroalkyl perfluorovinyl ethers (see Kirk-Othmer Encyclopedia of Chemical Technology, Fourth Edition, page 672) involves firstly the reaction of a fluoroalkyl carboxylic acid fluoride with hexafluoropropylene oxide to form an intermediate fluoroalkyl 2-alkoxypropionic acid fluoride as shown by the following equation:

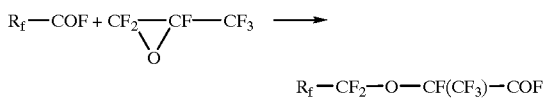

$R_f\text{—}CF_2\text{—}O\text{—}CF(CF_3)\text{—}COF$ wherein $R_f$ is fluorine or a fluorine-containing organic radical.

This intermediate fluoroalkyl 2-alkoxypropionic acid fluoride, after purification by distillation or other means, is then defluorocarbonylated by treatment with a dry alkali carbonate to form a fluoroalkyl perfluorovinyl ether as shown by the following equation:

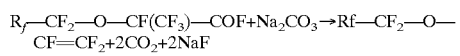

where $Na_2CO_3$ is used as an example of the alkali carbonate. In a typical process, the solid impurities such as NaF and unreacted $Na_2CO_3$ are then removed by filtration as by passing through a bag filter, and the $CO_2$ is removed by scrubbing with an alkali solution such as NaOH or KOH solution to form the corresponding alkali carbonate. KOH is preferred because of improved solubility. Water may then be removed as by passage through molecular sieves or by other means, and the dried crude fluoroalkyl perfluorovinyl ether is further purified as required for its intended use, typically by distillation to remove high and low-boiling impurities.

The removal of $CO_2$ by alkali scrubbing is costly for a number of reasons. Since there is a large amount of $CO_2$ produced, there is a large consumption of alkali and a large waste disposal problem for the alkali carbonate solution which is contaminated with fluorine-containing organic impurities. In addition, there is a significant yield loss, perhaps 1 to 5%, of expensive fluorochemical product caused by a combination of solubility in the waste scrubbing solution and some reactions of the fluoroalkyl perfluorovinyl ether with the alkali.

There is a need for a method for separation of part or essentially all of the $CO_2$ from the fluoroalkyl perfluorovinyl ethers reaction product with a minimum or elimination of alkali scrubbing, and without introducing new chemicals into the system.

It is also known to carry out polymerizations of fluorinated monomers in media comprising $CO_2$. See, for example, U.S. Pat. No. 5,674,957. Unreacted monomers from such processes are desirably recovered from mixtures with $CO_2$ for recycle to the polymerization reaction.

DESCRIPTION OF THE RELATED ART

The use of semipermeable membranes to separate gases other than $CO_2$ and fluorinated compounds, e.g., fluoroalkyl perfluoro vinyl ethers, is well known. Many of the separations disclosed in the literature are based on polyimide membranes. For example, Kim et al., "Relationship between Gas Separation Properties and Chemical Structure in a Series of Aromatic Polyimides", Journal of Membrane Science, 37 (1988), 45–62, discloses various polyimide structures tested for a number of gas separations. The present invention is not limited to a particular polyimide structure.

Many other such references describe suitable polyimide structures for gas permeation. U.S. Pat. No. 5,015,270 discloses a process for separation of gases using a polyimide membrane having phenylindane residues incorporated in the polyimide backbone chain. A preferred polyimide is "MATRIMID" 5218 polyimide resin, made by Ciba-Geigy and based on 5(6)-amino-1-(4'-aminophenyl)-1,3-trimethylindane. Examples to demonstrate selectivity were made with common atmospheric gases ($O_2$, $N_2$, $CO_2$, He).

U.S. Pat. No. 5,085,676 discloses a process for preparing a multicomponent membrane comprising a porous polymeric substrate and a separating layer of various polyimide or other structures. Example 40 utilizes "MATRIMID" 5218 as the separating layer and "ULTEM" 1000, a polyetherimide made by GE as substrate. Its selectivity was measured with $O_2/N_2$ mixtures.

U.S. Pat. No. 5,042,992 discloses a novel class of polyimides based on a partially fluorinated polyimide. It is said to be useful for making semipermeable membranes which have a high permeability and acceptable selectivity for $CO_2$ from mixtures of $CO_2$ and methane. The examples used to determine selectivity were either made using pure $CO_2$ and methane, a mixture of 30% $CO_2$ and 70% methane, or of 10% $CO_2$ and 90% methane.

U.S. Pat. No. 5,120,329 discloses a method for providing a controlled atmosphere in a food storage facility using a semipermeable membrane which has a higher permeability to $CO_2$ than to nitrogen. Typical $CO_2$ levels are given as about 0 to 20%, with 2% $CO_2$ used as the dividing line between low and high concentrations for various applications. Polyimide membranes are cited as examples of suitable membranes for this application.

In an article by Schell et al, "Membranes can Efficiently Separate $CO_2$ from Mixtures", Oil & Gas Journal, Aug. 15, 1983, page 83, an example is given of removing low concentrations of $CO_2$ from a refinery off-gas containing hydrogen by using a commercially available but unspecified membrane that allows $CO_2$ to permeate more rapidly than hydrogen. A two-stage membrane system was required to reduce the $CO_2$ concentration from 6% to 0.2% (60,000 ppm to 2000 ppm), with 50% of the hydrogen still retained in the non-permeate stream.

SUMMARY OF THE INVENTION

In accordance with the invention, a process is provided for separating carbon dioxide from an unsaturated fluorinated compound carbon dioxide mixture comprising contacting the unsaturated fluorinated compound carbon dioxide mixture with a semipermeable membrane to form at least one exit stream having an increased concentration of carbon dioxide and at least one other exit stream having a reduced concentration of carbon dioxide. Preferably, the membrane is a polyimide or a polyaramid membrane.

The process is preferably employed for separating carbon dioxide from mixtures comprising a compound selected from the group consisting of $CF_2=CF-R$ wherein R is F, Cl, $R_f$ or $O-R_f$ and $R_f$ is perfluoroalkyl containing 1–5 carbon atoms. When R is $O-R_f$, $CF_2=CF-R$ is preferably selected from perfluoropropyl perfluorovinyl ether (PPVE), perfluoromethyl perfluorovinyl ether (PMVE) and perfluoroethyl perfluorovinyl ether (PEVE). Another preferred unsaturated fluorinated compound is tetrafluoroethylene.

In a preferred form of the invention, the semipermeable is a polyimide membrane and has phenylindane residues incorporated in the polyimide backbone chain.

In a preferred process in accordance with the invention, the exit stream with increased concentration of carbon dioxide contains less than about 10% by weight of the unsaturated fluorinated compound present in the original unsaturated fluorinated compound carbon dioxide mixture.

DETAILED DESCRIPTION

Figure 1:
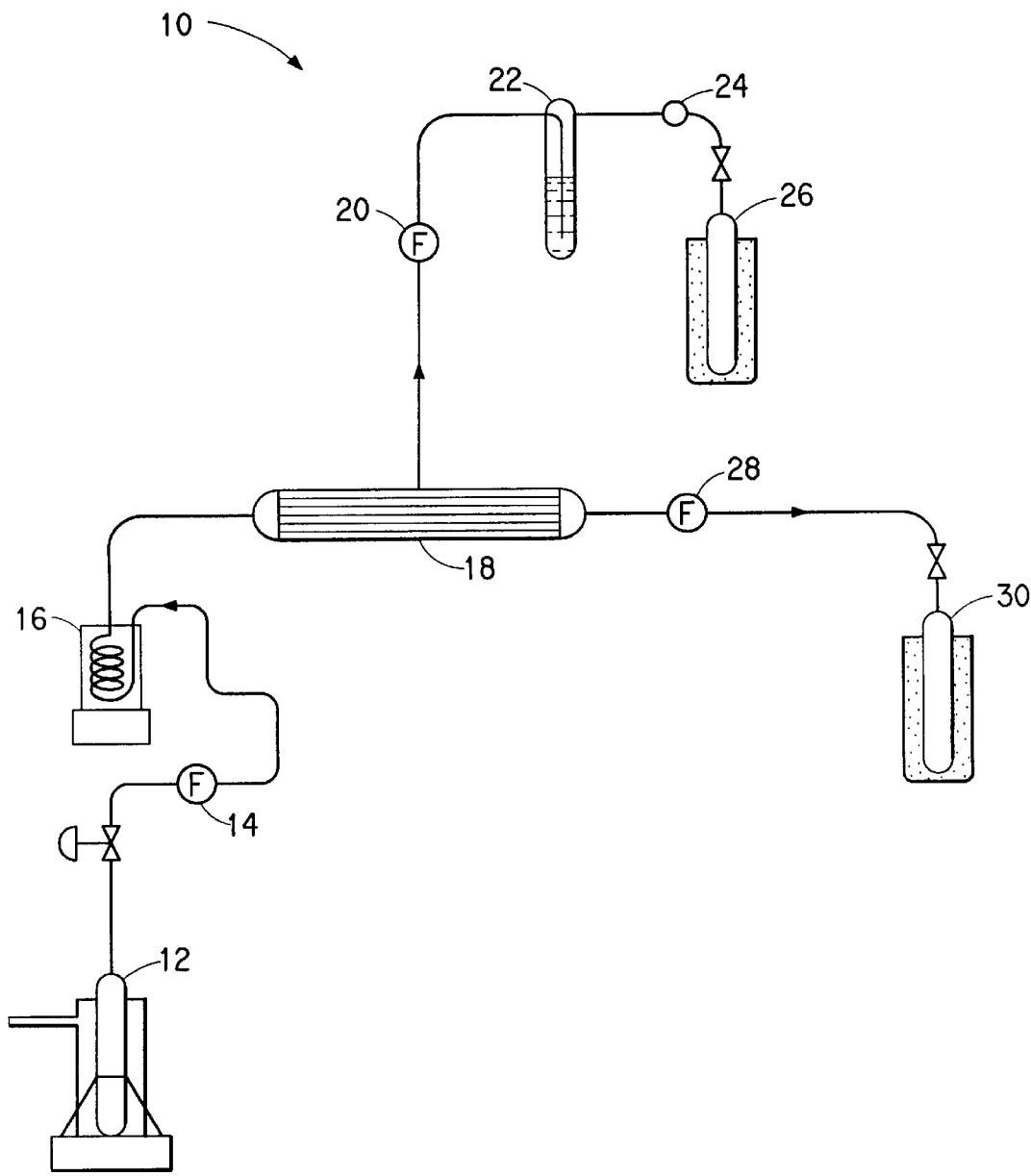
FIG. 1 is a diagrammatical view of laboratory scale apparatus useful for illustrating an embodiment of the present invention.

In this application, "unsaturated fluorinated compound" refers to unsaturated perhalogenated compounds containing fluorine, and preferably to compounds of the formula $R-CF=CF_2$, wherein R is F, Cl, $R_f$ or $O-R_f$ and $R_f$ is perfluoroalkyl containing 1–5 carbon atoms. Preferred R in compounds in the carbon dioxide mixtures for the practice of the present invention are R, $R_f$ and $O-R_f$. When R is $O-R_f$, preferred fluorinated compounds include perfluoropropyl perfluorovinyl ether (PPVE), perfluoromethyl perfluorovinyl ether (PMVE) and perfluoroethyl perfluorovinyl ether (PEVE). Another preferred fluorinated compound is tetrafluoroethylene (TFE). Another preferred fluorinated compound is hexafluoropropylene (HFP).

The fluorinated compound component of the unsaturated fluorinated compound carbon dioxide mixture from which $CO_2$ is removed by the process of the present invention is comprised of at least one fluorinated compound. Thus, the fluorinated compound component of the unsaturated fluorinated compound carbon dioxide mixture can be a mixture of unsaturated fluorinated compounds. Such mixtures include, for example, TFE/HFP, TFE/PAVE, and TFE/HFP/PAVE, wherein PAVE is perfluoro(alkyl vinyl ether). In the foregoing mixtures, PAVE can be a single compound or a PAVE mixture, e.g., a mixture of perfluoro(methyl vinyl ether) and perfluoro(propyl vinyl ether), or, e.g., a mixture of perfluoro (ethyl vinyl ether) and perfluoro(propyl vinyl ether). One skilled in the art will recognize that compounds other than those defined above, i.e., $CF_2=CF-R$, can be present in the mixture. Such other compounds can contain fluorine or can be fluorine-free, and may or may not be separated from $CO_2$ by the process of the present invention.

In accordance with the present invention, a mixture of unsaturated fluorinated compound and carbon dioxide is contacted with a semipermeable membrane to form two exit streams, one of which has an increased concentration of carbon dioxide ($CO_2$) and the other exit stream has a reduced concentration of carbon dioxide. Usually, the reduced $CO_2$ stream is the "non-permeate" stream, often called the "reject" stream, and does not pass through the membranes whereas the "permeate" stream passes through the membrane and has increased $CO_2$ content. Typically, the stream with reduced $CO_2$ content is recovered, i.e., shipped or sold in the form recovered, processed by contact with other semipermeable membranes, or further processed by conventional means to achieve additional separation or recovery/removal of a desired component. The fluorinated compound, e.g., vinylether, enriched in $CO_2$ can be recycled to earlier stages in the purification process, subjected to further purification before recycling, blended with fluorinated compounds of the same type to be used for less demanding markets, or disposed of by incineration or other means as permitted by environmental regulations. When the process of the invention is used in conjunction with polymerizations of fluorinated monomers in $CO_2$, the monomer concentration in the reactor discharge stream can be increased for recycle to polymerization, a step that usually would not require a very high monomer concentration. Other components, organic or inorganic, may be present during the contacting step of the instant invention.

The membrane separation device useful in the present invention can be any such device as known in the art and may be in any shape which has a feed side and a permeate side. Included in this description are membranes which can be formed into films (with or without support), tubular devices, spiral wound devices, hollow fibers and the like.

The semipermeable membrane useful in the instant invention prefereably is polyimide membrane or polyaramid membrane. Such membrane may be made of any polyimide or polyaramid material capable of preferentially passing the $CO_2$ relative to the unsaturated fluorinated compounds. That is, the ratio of permeation rates of the $CO_2$ to that of the unsaturated fluorinated compounds should be greater than 1. Obviously, the higher the ratio, the more efficient will be the separation process.

Polyimide membranes typically used in commercial use for conventional gas separations may be used. Preferably, the polyimide has phenylindane residues incorporated in the polyimide backbone chain. One membrane of this type is "MATRIMID" 5218 polyimide resin, manufactured by Ciba-Geigy and based on 5(6)-amino-1-(4'-aminophenyl)-1, 3-trimethylindane. The membrane may be a composite of a porous substrate and the polyimide resin. For example, hollow fibers of "Ultem" 1000, a polyetherimide made by General Electric, are a particularly suitable support for "Matrimid" 5218. Such membranes and their manufacture are disclosed in U.S. Pat. No. 5,085,676. Polyaramid membranes that can be used include those of the types disclosed in U.S. Pat. No. 5,085,774. As in known permeation separation process, parameters which are usually considered as variables to enhance the separation process are the temperature, the pressure differential and average pressure ratio between the feed side of the membrane and the permeate side of the membrane, and the residence time of the feed stream on the feed side of the membrane and the residence time of the permeate on the permeate side of the membrane. In the instant invention, these parameters may be varied to enhance the separation so long as the values selected are not damaging to the membrane material. Temperature can be any convenient temperature, usually from about −50 to 150° C. The primary temperature limitations are that the temperature should be below any temperature at which the membrane is affected adversely and above the dew point of the fluorocarbon. Preferably, the temperature range will be from about 0 to about 75° C.

The pressure differential between the feed side of the membrane and the permeate side is preferably at least about 0.1 atmosphere (10 kPa). The process may be operated at a lesser pressure differential but the separation process will be slower. The pressure differential can be the result of higher pressure on the feed side of the semipermeable membrane or the result of reduced pressure on the permeate side of the membrane or a combination of both. Useful feed pressures can vary substantially with the mode in which the membrane device is employed and with the materials being separated. For hollow fiber membranes, for example, feed pressure might be as high as 1000 psig (7 MPa) for feed to the outside of the fibers (shell-side feed) but might be limited to 200–250 psig (1.5–1.8 MPa) for bore-side feed. Additionally, choice of pressure should be consistent with safe handling of the various streams.

The present process can be carried out as a batch process or as a continuous process. Since this permeation separation process is a differential process producing a substantial reduction in $CO_2$, multiple pass or multiple stage processes may be the most efficient system to achieve very high purity fluorocarbons. In such multiple stage arrangements, an output stream from one stage can be fed to another stage either as the primary feed to that other stage or as a recycle stream. The term "stage" as used in the present application is intended to encompass a stage in which gases are fed to a separate membrane separation device or a pass in which gases are returned to the same device. Preferably, at least about 50%, more preferably at least about 75%, by weight of the $CO_2$ present is removed in a stage of the process. When low or trace levels of $CO_2$ are present, removal to less than a few ppm can be achieved in a one or two pass process. Because of the efficient separation of $CO_2$ in preferred processes in accordance with the invention, the process is particularly advantageous for applications in which the unsaturated fluorinated compound mixture contains significant levels of $CO_2$, especially mixtures containing at least about 10% by weight $CO_2$. The present invention provides separation without the purchase and addition of extraneous materials and without creating additional waste disposal problems.

Preferred processes in accordance with the invention can provide low "losses" of the unsaturated fluorinated compounds. "Loss" is determined from the weight of the unsaturated fluorinated compound in the stream with increased carbon dioxide concentration (usually the permeate stream) in relation to the weight of the unsaturated fluorinated compound present in the original unsaturated fluorinated compound carbon dioxide mixture. Preferably, the exit stream with increased concentration of carbon dioxide contains less than about 10% by weight, more preferably less than about 5 percent, and most preferably less than about 2%, of the unsaturated fluorinated compound present in the original unsaturated fluorinated compound carbon dioxide mixture. The aforesaid low losses can be achieved in multiple stage processes, but preferably are achieved in a single stage.

Compared to known processes which employ caustic scrubbers for removal of $CO_2$, the process in accordance with the invention not only eliminates the need for a caustic scrubber, eliminating its capital cost, but also eliminates the required consumption of caustic and its substantial annual cost. The process also eliminates the need to remove water from the product after scrubbing. From an environmental standpoint, the amount of waste products for disposal is also substantially reduced. Compared to known processes for the manufacture of PPVE, a yield improvement for the PPVE of perhaps 1 to 5% is also achievable because of the elimination of caustic scrubber solubility and reaction losses.

The following examples are presented for illustrative purposes only, and in no way are intended to limit the inventive process.

Example 1

This example illustrates removing $CO_2$ from a mixture of perfluoromethyl perfluorovinyl ether (PMVE) and $CO_2$.

With reference to FIG. 1 illustrating laboratory scale apparatus 10 for carrying out the present invention, a 788 gram mixture of 313 gram $CO_2$ and 475 gram PMVE (40 weight % $CO_2$/60 weight % PMVE; or 71 mol % $CO_2$/29 mol % PMVE) is prepared by charging the ingredients into an evacuated pressure cylinder 12 at 20–21° C and 475 psig (3380 kPa). As illustrated in FIG. 1, this is connected to flow measuring device 14, to a hot water heated coil 16 and then to the inlet side of a permeation separator 18. The permeation separator 18 and input line is heated so that the separation is performed at 60° C. The feed rate is 5 grams per minute. The permeation separator uses a commercial polyimide membrane in the form of 360 hollow fibers 73 cm long having outside diameter of 160 $\mu$m and bore diameter of 90 $\mu$m. The membrane used is Ciba Geigy's "MATRIMID" 5218 polyimide skin covering a bulk porous fiber wall made of General Electric's "ULTEM" 1000.

The permeate gas is fed to a flowmeter 20, sparged into a tank 22 containing 3 weight % sodium hydroxide in water at 50° C., to a second flowmeter 24 and then to a dry ice trap 26 held at −60° C. The non-permeate gas or product is fed to a flowmeter 28 and to a receiving tank 30 held at −180° C. by liquid nitrogen. The feed concentration changes from the original value of 40 weight % $CO_2$ to very low values during the course of the test, permitting the evaluation of the separation system under a variety of inlet feed concentrations. Under conditions of the test, the feed pressure into the permeator is initially about 90 psig (725 kPa), and the pressure at the non-permeate discharge is about 75 psig (620 kPa). The pressure on the permeate side of the permeator is about 8 psig (160 kPa). While these pressures drop slightly during the course of the test, the pressure differential across the membrane is maintained throughout the test.

The entire trial took about 2.5 hours. The nominal gas residence time inside the permeator hollow fibers is calculated to be about 0.4 seconds. The actual feed into the permeator is a total of about 730 grams, and is split into a 228 gram permeate stream consisting of about 100 weight %

$CO_2$ and a 456 gram non-permeate stream estimated to contain about 11 to 14 weight % $CO_2$. This compares to an as-charged composition of 40 weight % $CO_2$. The overall material balance is calculated to be about 98% complete. Remarkably, no measurable amount of PMVE is observed flowing out of the caustic bath or is found in the −60° C. dry ice trap. Total fluoride content of the caustic from the caustic bath is found to be below 10 ppm in subsequent trials. Therefore, it is concluded that no measurable amount of PMVE is lost as permeate.

Example 2

To simulate the performance of the process of the invention in a two-stage purification system, a second trial is made in which non-permeate product from Example I is used as the feed to the permeator.

Using the same 360 fiber permeator 18 as in Example 1 at 60° C. and with a nominal 75 psig (620 kPa) inlet pressure and 65 psig (550 kPa) outlet pressure, 424 grams of feed are processed over a 2 hour period. As in the prior Example, while permeate flow into the caustic bath is appreciable, the flow after scrubbing with caustic solution is negligible, indicating that the permeate is essentially pure $CO_2$. A total of 59 grams of permeate is captured in the scrubbing solution. The non-permeate receiver captures 311 grams of product. Another 40 grams of product is estimated to have been lost due to insufficient liquid nitrogen cooling and an equipment malfunction, making the overall material balance about 87% complete. The product is estimated to contain about 4.5 to 5 weight % $CO_2$, based on the $CO_2$ balance and fmal receiver vapor pressure, compared to the estimated 11 to 14 weight % feed.

Example 3

This example illustrates the removal of $CO_2$ from perfluoropropyl perfluorovinyl ether (PPVE) containing byproduct $CO_2$, using a two-stage permeator system composed of commercial scale permeator units. Four permeators are used which generally have the same construction and the same materials as in Examples 1 and 2 but having 80,000 fibers in each unit. The four permeators are connected so that there are two sets of permeators connected in series with the two sets being connected together in parallel.

A gas composed of 71.2 weight % PPVE and 28.8 weight % $CO_2$ is fed to the permeators at a rate of 297 lb/hr and a pressure of 69 psig (580 kPa). The permeate is 83 lb/hr of a gas at 0 psig (105 kPa) containing 99.96 weight % $CO_2$ and 0.04 weight % PPVE. The non-permeate is 214 lb/hr of a gas at 57 psig (495 kPa) containing 98.8 weight % PPVE and 1.2 weight % $CO_2$. In this process, nearly 97% of the $CO_2$ is removed by the above permeation separation process, and the non-permeate PPVE is more pure than typically obtained by caustic scrubbing in existing commercial processes.

Example 4

A permeator similar to that of Example 1 except that fiber length is 41 cm is used to separate a mixture of 48 wt % TFE and 52 wt % $CO_2$ at 23°±2° C. The experimental arrangement differs from that shown in FIG. 1. With reference to FIG. 1, the TFE/$CO_2$ source 12 is a cylinder initially charged with 3800 g of the gas mixture at 420 psig (3.0 MPa) and recharged only as necessary. The cylinder is equipped with a pressure regulator set to deliver the feed gas at 60 psig (0.52 MPa). A GC sample is taken between the mass flow meter 14 and the permeator 18. The heated coil 16 is not used. On the reject (i.e., non-permeate) side, the exit pressure is controlled by a throttle valve to create a range of feed-side pressure differences, Δp. The reject stream passes through volumetric flow meter 28 to atmospheric pressure. Receiving tank 30 is not used. On the permeate side, the permeate passes through volumetric flow meter 20 to atmospheric pressure. Tank 22, flowmeter 24, and trap 26 are not used. GC samples are taken in both the permeate and reject streams upstream from the flow meters. The combined flow and GC measurements lead to a good mass balance, enhancing confidence in the flow and GC data. Flow rate and compositional data summarized in Table 1 show that a TFE/$CO_2$ stream rich in $CO_2$ can be separated effectively with a polyimide membrane. "Loss" is the fraction (%) of total TFE flow that is in the permeate stream. There is no evidence of reaction between the membrane and the highly reactive TFE. I.e., there is no evidence of attack of the membrane by the TFE, and no evidence of TFE polymerization which is known in $CO_2$ media (no initiation by the membrane).

TABLE 1

Separation of TFE and $CO_2$ with Polyimide Membrane

| Δp | | TFE in Reject Stream | | TFE in Permeate Stream | |
|---|---|---|---|---|---|
| (psi) | (kPa) | Rate (g/min) | Purity (wt %) | Rate (g/min) | Loss (%) |
| 59.0 | 407 | 8.604 | 60.0 | 0.0520 | 0.60 |
| 25.0 | 172 | 5.233 | 71.4 | 0.0786 | 1.48 |
| 12.8 | 88 | 3.912 | 82.7 | 0.0967 | 2.41 |
| 5.6 | 39 | 1.977 | 91.2 | 0.1046 | 5.02 |
| 2.7 | 19 | 0.960 | 95.8 | 0.1225 | 11.3 |
| 1.1 | 8 | 0.334 | 98.5 | 0.1204 | 26.5 |

Example 5

The procedure of Example 4 is essentially repeated, except that a permeator made with polyaramid hollow fibers is used and feed pressure values of 100 and 145 psig (0.79 and 1.10 MPa) are tested in addition to 60 psig. The fiber membranes are made generally according to Examples 9–12 of U.S. Pat. No. 5,085,774 and the permeator incorporates 200 such fibers 73 cm long having outside diameter of 200 μm and bore diameter of 80 μm. Flow rate and compositional data summarized in Tables 2–4 show that a TFE/$CO_2$ stream rich in $CO_2$ can be separated effectively with a polyaramid membrane. Note, in comparison with Example 4, that polyaramid provides less "loss" at a given purity but has lower productivity despite higher membrane area. However, productivity can be enhanced by increased feed pressure without significant impact on loss. There is no evidence of reaction between the membrane and the highly reactive TFE. I.e., there is no evidence of attack of the membrane by the TFE, and no evidence of TFE polymerization which is known in $CO_2$ media (no initiation by the membrane).

TABLE 2

TFE/$CO_2$ Separation at 60 psig with Polyaramide Membrane

| Δp | | TFE in Reject Stream | | TFE in Permeate Stream | |
|---|---|---|---|---|---|
| (psi) | (kPa) | Rate (g/min) | Purity (wt %) | Rate (g/min) | Loss (%) |
| 4.8 | 33 | 0.3409 | 56.0 | 0.00068 | 0.20 |
| 2.8 | 19 | 0.2140 | 60.7 | 0.00071 | 0.33 |
| 1.8 | 12 | 0.1440 | 66.0 | 0.00069 | 0.48 |
| 1.0 | 7 | 0.0937 | 78.9 | 0.00079 | 0.83 |
| 0.5 | 3 | 0.0559 | 85.5 | 0.00073 | 1.29 |

TABLE 3

TFE/CO$_2$ Separation at 100 psig with Polyaramide Membrane

| Δp | | TFE in Reject Stream | | TFE in Permeate Stream | |
|---|---|---|---|---|---|
| (psi) | (kPa) | Rate (g/min) | Purity (wt %) | Rate (g/min) | Loss (%) |
| 4.9 | 34 | 0.5435 | 58.1 | 0.00110 | 0.20 |
| 3.7 | 23 | 0.4318 | 60.5 | 0.00112 | 0.26 |
| 2.7 | 19 | 0.3358 | 63.6 | 0.00120 | 0.36 |
| 1.8 | 12 | 0.2532 | 69.7 | 0.00123 | 0.48 |
| 0.8 | 6 | 0.1398 | 82.1 | 0.00137 | 0.97 |
| 0.5 | 3 | 0.0972 | 90.2 | 0.00149 | 1.51 |

TABLE 4

TFE/CO$_2$ Separation at 145 psig with Polyaramide Membrane

| Δp | | TFE in Reject Stream | | TFE in Permeate Stream | |
|---|---|---|---|---|---|
| (psi) | (kPa) | Rate (g/min) | Purity (wt %) | Rate (g/min) | Loss (%) |
| 5.1 | 35 | 0.8438 | 59.9 | 0.00192 | 0.23 |
| 4.2 | 29 | 0.7101 | 62.2 | 0.00196 | 0.27 |
| 3.2 | 22 | 0.5777 | 65.7 | 0.00196 | 0.34 |
| 2.0 | 14 | 0.4086 | 72.9 | 0.00210 | 0.51 |
| 1.0 | 7 | 0.2393 | 84.0 | 0.00233 | 0.96 |
| 0.5 | 3 | 0.1509 | 89.8 | 0.00227 | 1.49 |

Example 6

This example illustrates separation of TFE and CO$_2$ using a two-stage permeator setup. Two permeators similar to that described in Example 4 are arranged in series, with the reject stream from the first permeator being the feed stream to the second permeator. Feed pressures $p_1$ to stage 1 of 60, 100 and 140 psig (0.52, 0.79, and 1.07 MPa) are tested at various total Δp with Δp regulated so that $\Delta p_1 = 2\Delta p_2$, wherein the subscripts identify the stage. Tables 5 and 6 show data for total Δp of 6 and 12 psi (41 and 83 kPa). Note that total "loss" can be limited to first-stage "loss" by recycling second-stage permeate with appropriate pressure increase to the first-stage feed, which is especially convenient when the second-stage permeate composition is close to that of the first-stage feed.

TABLE 5

Data for Stage 1 of Example 6

| $p_1$ | $\Delta p_1$ | TFE in Reject Stream | | TFE in Permeate Stream | |
|---|---|---|---|---|---|
| (MPa) | (kPa) | Rate (g/min) | Purity (wt %) | Rate (g/min) | Loss (%) |
| 0.52 | 27.6 | 1.078 | 87.2 | 0.0333 | 2.99 |
| 0.52 | 55.2 | 2.073 | 75.1 | 0.0350 | 1.66 |
| 0.79 | 27.6 | 2.121 | 88.9 | 0.0678 | 3.10 |
| 0.79 | 55.2 | 3.563 | 78.0 | 0.0544 | 1.50 |
| 1.07 | 27.6 | 2.082 | 94.7 | 0.1256 | 5.69 |
| 1.07 | 55.2 | 4.778 | 82.4 | 0.1043 | 2.14 |

TABLE 6

Data for Stage 2 of Example 6

| $p_2$ | $\Delta p_2$ | Stream TFE Purity (wt %) | | TFE in Permeate Stream | |
|---|---|---|---|---|---|
| (MPa) | (kPa) | Reject | Permeate | Rate (g/min) | Loss (%) |
| 0.49 | 13.8 | 89.3 | 22.5 | 0.0072 | 0.67 |
| 0.46 | 27.6 | 81.4 | 4.2 | 0.0063 | 0.30 |
| 0.77 | 13.8 | 92.6 | 18.0 | 0.0152 | 0.71 |
| 0.74 | 27.6 | 85.3 | 3.7 | 0.0127 | 0.36 |
| 1.04 | 13.8 | 95.9 | 45.2 | 0.0248 | 1.19 |
| 1.01 | 27.6 | 90.1 | 5.7 | 0.0248 | 0.53 |

Example 7

The experimental arrangement of Example 6 is used to generate a feed stream to the second-stage permeator that is low in CO$_2$. This is done by feeding a TFE/CO$_2$ mixture containing 50.3 wt % of CO$_2$ to the first stage at 180 psig (1.34 MPa), using low $\Delta p_1$ of 1.0 and 0.8 psi (6.9 and 5.5 kPa), and using reduced pressure (partial vacuum) on the permeate side of the first stage permeator. The resulting streams containing 2.96 and 1.14 wt % of CO$_2$, respectively, are processed through the second-stage permeator at $\Delta P_2$ of 0.5 psi (3.4 kPa). Data in Table 7 show that the process of this invention can be used effectively to separate TFE and CO$_2$ even when the CO$_2$ concentration is low to obtain TFE of even higher purity.

TABLE 7

Polyimide Membrane at Low CO$_2$ Concentration (Example 7)

| CO$_2$ Conc. (wt %) | | TFE Rate (g/min) | | CO$_2$ Rate (g/min) | | Removed |
|---|---|---|---|---|---|---|
| Feed | Reject | Feed | Reject | Feed | Reject | CO$_2$ (%) |
| 2.96 | 1.03 | 1.589 | 1.582 | 0.0485 | 0.0165 | 66.0 |
| 1.14 | 0.58 | 1.172 | 1.148 | 0.0135 | 0.0067 | 50.4 |

What is claimed is:

1. A process for separating carbon dioxide from an unsaturated fluorinated compound carbon dioxide mixture comprising one or more stages in which a feed stream of said unsaturated fluorinated compound carbon dioxide mixture is contacted with a semipermeable membrane to form at least one exit stream having an increased concentration of carbon dioxide and at least one exit stream having a reduced concentration of carbon dioxide, said process in at least one of said one or more stages causing said exit stream with increased concentration of carbon dioxide to contain less than about 5% by weight of the unsaturated fluorinated compound present in said feed stream.

2. The process of claim 1 wherein said unsaturated fluorinated compound comprises a compound of the formula R—CF=CF$_2$, wherein R is F, Cl, R$_f$ or O—Rf and R$_f$ is perfluoroalkyl containing 1–5 carbon atoms.

3. The process of claim 1 wherein said unsaturated fluorinated compound comprises tetrafluoroethylene.

4. The process of claim 1 wherein said semipermeable membrane comprises a membrane selected from the group consisting of polyimide membranes and polyaramid membranes.

5. The process of claim 1 wherein said semipermeable membrane comprises a polyimide membrane having phenylindane residues incorporated in the polyimide backbone chain.

* * * * *